United States Patent [19]

Hirabayashi et al.

[11] 4,122,605
[45] Oct. 31, 1978

[54] SOMATIC ELEMENT OF SINGLE CRYSTALLINE SAPPHIRE CERAMICS

[75] Inventors: Masaya Hirabayashi, Yokaichi; Haruyuki Kawahara, Moriguchi; Yoshio Taniguchi, Gamo, all of Japan

[73] Assignee: Kyoto Ceramic Kabushiki Kaisha, Kyoto, Japan

[21] Appl. No.: 725,511

[22] Filed: Sep. 22, 1976

[51] Int. Cl.² ................................................. A61C 8/00
[52] U.S. Cl. ................................... 32/10 A; 128/92 D
[58] Field of Search ........ 32/10 A; 128/92 C, 92 CA; 3/1.9, 1.91, 1.911, 1.912, 1.913; 264/19, 65, 67, 341; 106/35, 45

[56] References Cited

U.S. PATENT DOCUMENTS

| 2,854,794 | 10/1958 | Luedeman | 264/67 |
| 3,753,775 | 8/1973 | Robinson et al. | 156/612 |

FOREIGN PATENT DOCUMENTS

| 1,083,769 | 9/1967 | United Kingdom | 3/1.9 |
| 1,334,584 | 10/1973 | United Kingdom | 128/92 CA |

OTHER PUBLICATIONS

143311C "Healing of Surface Cracks in Ceramics", Chemical Abstracts, vol. 77.

*Primary Examiner*—Louis G. Mancene
*Assistant Examiner*—John J. Wilson
*Attorney, Agent, or Firm*—Spensley, Horn & Lubitz

[57] ABSTRACT

This disclosure relates to a somatic element of single crystalline sapphire ceramics for use as an implant for dental surgery, orthopedic prosthetic surgery and the like, which element is excellent in mechanical strength, flexibility and affinity with its ambient tissue so much so that it eliminates a fear of development of bone cancer and facilitates the proliferation of uniform bone tissue around the somatic element implanted.

9 Claims, 5 Drawing Figures

SOMATIC ELEMENT OF SINGLE CRYSTALLINE SAPPHIRE CERAMICS

BACKGROUND OF THE INVENTION

1. Field of Invention

This invention relates to a somatic element of single crystalline sapphire ($\alpha$-Al$_2$O$_3$ :corundum) ceramics used as an implant for dental surgery or an implant for orthopedic surgery and to a method of manufacturing the same.

2. Prior art

Heretofore, metal (for example, stainless steel, Co—Cr alloy, metallic titanium, metallic tantalum, Ni—Cr alloy, etc.) has been used as a material in a somatic element of the kind described. However, the somatic element of such metal is in most cases inferior in so-called "affinity" with (adhesibility to, wettability with) its ambient tissue and in addition, there is a possibility of the somatic element tending to be ionized by saliva, secretion of the mouth, food, body fluids, blood and the like thereby producing harmful effects as a result of metallic ions in the human body. To cite a positive instance of such a fact, it is reported that in the case of stainless steel most generally used as a somatic element for orthopedic surgery, it is necessary to perform a repeated operation on the affected region to extract the element therefrom in a certain period of time after the operation. On the other hand, in the case of a somatic element of polycrystalline ceramics, the element is excellent in affinity with its ambient tissue and chemically highly stable, thereby having no necessity of extracting the element from the implanted region after the operation, but has the disadvantage of it being inferior in mechanical strength to a metallic member. In view of this fact, the present applicant has provided various inventions for improvements in the mechanical strength of a somatic element of ceramics. The somatic element proposed heretofore by the inventions is dependent upon the structure of the element itself for the postoperational strength of the implanted element. For example, in the previous U.S. patent application, Ser. No. 550,186, 1974, such structural consideration was given to the tightening force produced by threadedly fitting a nut over the top of a screw type implant pin of ceramics embedded in the bone tissue (and if necessary, over the bottom part of the pin that projects through the bone tissue) and used to fix the implant pin to the bone tissue so that the implant pin could cope with outer force such as repeated occlusal impact imparted to the pin after the implantation. Similarly, in the previous U.S. patent application, Ser. No. 674,688, 1975, by the present applicant, structural consideration was given to the manner that a screw type implant pin of ceramics was provided in the circumference with a horizontal flange, the horizontal flange acting as a stabilizing seat since the flange is fitted closely into the counterbore formed in a cortical bone (hard tissue) when the pin is threadedly inserted into the bone so that the pin could withstand the outer force to be later applied thereto.

SUMMARY OF THE INVENTION

This invention, which is from a viewpoint different from what has conventionally been considered, is intended to provide a somatic element of single crystalline sapphire ceramics ($\alpha$-Al$_2$O$_3$) which is better in mechanical strength, flexibility and affinity with its ambient tissue (particularly osteoplastic cells) than polycrystalline ceramics out of various ceramics.

Generally, polycrystalline ceramics, for example, a sample of polycrystalline alumina ceramics (a rod-shaped sample of 3mm in diameter and the same will apply hereinafter) shows bending strength of merely 2,500–3,500 kg/cm$^2$ because of its internal microstructure which permits the presence of impurities (binding agent, grain growth retarding agent, etc.) in the crystal grain boundary; while in contrast thereto, a sample of single crystalline sapphire ceramics has no such crystal grain boundary and is of a completely single crystalline structure, with the result that the latter type ceramics shows bending strength of the order of 10,000 kg/cm$^2$ and is far superior also in flexibility to polycrystalline ceramics. Furthermore, in the case of the polycrystalline ceramics, the presence of fine cavities in the crystal grain boundary prevents the affinity of the ceramics with its ambient tissue and tends to reduce the adhesibility of the ceramics to the ambient tissue; while the single crystalline ceramics, because it contains no such affinity retarding crystal grain boundary, is particularly excellent in affinity with the ambient tissue. By the way, as will later be described in detail, the single crystalline sapphire ceramics can be obtained in the rod-shaped, columnar, plate-shaped or similar form of single crystal of $\alpha$-Al$_2$O$_3$. Furthermore, when the ceramics is used for a somatic element, it can be cut and worked by a diamond grinder or the like into a desired shape adapted for a dental or an orthopedic surgical member for a broken bone such as for example, a screw type implant pin, blade type implant pin, pin type implant pin, compression plate, with the result that sharp end edges are formed on the external of the element and at the same time similarly sharp wavelike scars by the cutting and working are left on the worked surface. It is believed that these edged portions not only reduce affinity of the element with the bone tissue around the portions, but if left implanted in the bone tissue for a long time, may lead to the development of bone cancer because of the stress repeatedly imparted by the edged portions to the bone tissue. And also, the presence of the scars formed by cutting and shaping makes it possible for a new bone tissue to partially proliferate in the edged portions alone and forms a cause of hampering the growth of a uniform bone tissue. In addition to such a fear and drawback coming from a medical viewpoint alone, the presence of the scars provides stress concentration in the scarred region in the case of such a homogeneous body as single crystal to thereby make a rapid reduction in the strength of the element to a degree of about 6,000 kg/cm$^2$. Accordingly, this invention is directed to rounding the edged ends into a smooth surface to eliminate a possibility of developing cancer and to actuate the uniform development of a bone tissue by removing the scars left on the worked surface of the element by high-temperature chemical polishing with molten salt or high-temperature fire polishing with hydrogen after the working of the element and further to restoring bending strength inherent to single crystal or to producing strength greater than that.

BRIEF DESCRIPTION OF THE DRAWINGS

A description will now be made of a somatic element of the invention and a method of manufacturing the element, the surface state of the element in its stage of manufacture, and the bending strength of the element with reference to preferred embodiments of the invention shown by way of example in the accompanying drawings wherein.

DETAILED DESCRIPTION OF THE INVENTION

Figure 1:
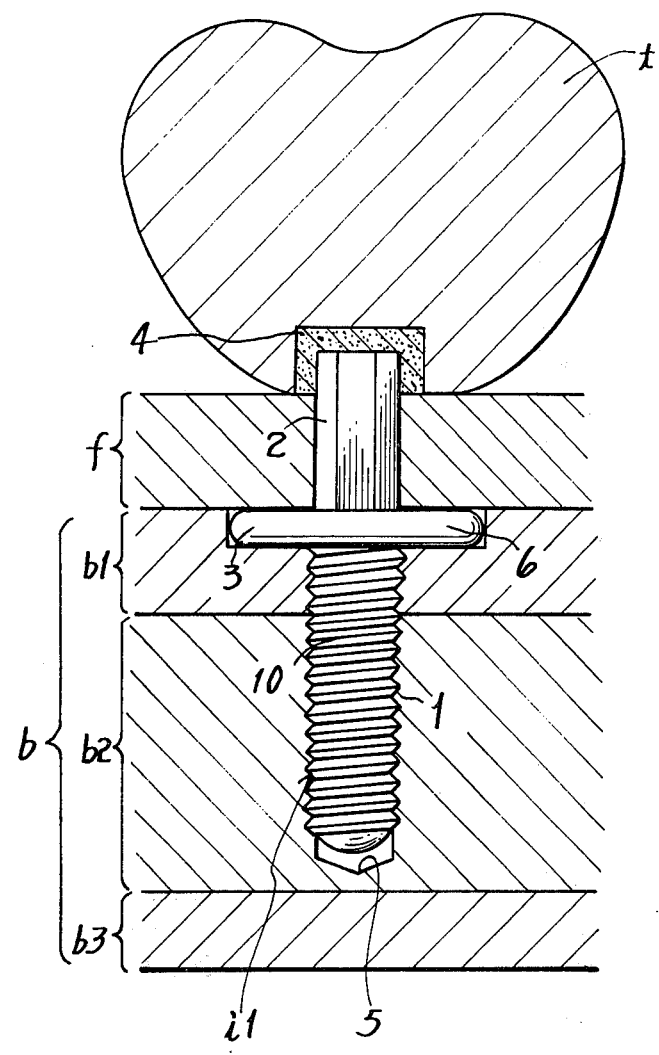
FIG. 1 is a longitudinal sectional view of the element in accordance with the teachings of the present invention used as a dental implant.

(I) Method of manufacturing a single crystalline sapphire material

A material of $\alpha$-$Al_2O_3$ in a crucible is melted by high-frequency induction heating and a single crystalline sapphire seed was steeped in the molten material. When the seed was raised from the molten material, a single crystalline solid of $\alpha$-$Al_2O_3$ in the form of a rod was obtained from the molten material by surface tension of the molten material. This method is well known as a Czochralski process, but the use of a single crystalline continuous formation device called "EFG process" which is an improvement over the Czochralski process would be industrially advantageous. According to this EFG process, a die excellent in wettability with respect to the molten material is steeped in the molten material and the seed is raised from the molten material through the die, with the result that a single crystalline solidified mass of a desired sectional configuration, for example, a rod-shaped, plate-shaped, tubular or the like configuration can be obtained. For example, the surface state of a rod-shaped single crystalline material 3mm in diameter which was raised at a velocity of 20mm/min. from the molten material at a temperature of 2050° C in an argon atmosphere according to the EFG process is smooth but a nonuniform layer is dispersed, and this single crystalline material was on the order of 8,000–10,000 kg/cm$^2$ in bending strength.

(II) Cutting and working of somatic element

A single crystalline material was cut and shaped by a diamond grinder into a somatic element of a desired configuration. For example, the exterior of the single crystalline material in Item (I) which was machine cut by diamond grinder No. 250 had very sharp edges and the surface of the material was rough because of the presence of the cutting scars and the bending strength of the material was on the order of 6,000 kg/cm$^2$.

(III) Removal of cutting scars

As described, sharp-edged and steep wavelike cutting scars are left on the surface of the somatic element of single crystal after the cutting and working, and the scars are removed to round out the sharp edges and provide a smooth surface and to restore and improve the bending strength of the element in the following manner.

(III-A) High-temperature fire polishing with hydrogen

A single crystalline material after cutting and working was subjected to high-temperature fire polishing with hydrogen at 1200°–1900° C, preferably 1,500–1,700° C to thereby round out the sharp edges and smoothen the surface of the material. For example, the single crystalline material after the cutting and working was subjected to high-temperature polishing at a temperature of 1550° C for 20 minutes in an atmosphere of reduced gas ($H_2$). The surface of the material thus treated had sharp edges removed therefrom and was far more smooth than that of the material left cut and worked but there were still left certain irregularities. The bending strength of this material was restored to about 9,000–10,000 kg/cm$^2$. Furthermore, if the temperature is lower than 1,200° C, surface polishing is not carried out sufficiently and if it is higher than 1,900° C, surface polishing is carried out so very briskly that deformation begins at the single crystal face of a formed body itself and the body changes markedly in configuration, being rendered unusable. The temperature is preferably 1,500°–1,700° C.

(III-B) High-temperature chemical polishing with molten salt

When the single crystalline material after cutting and working was steeped in the molten salt of one selected from borate, molybdate ($Na_2Mo_2O_7$, $PbMoO$, etc.), tungstate ($Na_2W_2O_7$, $Li_2W_2O_7$, $PbWO_4$, etc.), and vanadium pentoxide ($V_2O_5$), it becomes easy to melt because the larger cutting scars provide the larger surface area of reaction, and the whole surface becomes nearer to smoothness. For example, the single crystalline material after cutting and working was steeped in a molten salt of borax at 1,100° C for about 10 minutes and was subject to a high-temperature chemical polishing with molten salt. The material thus treated provides a more regular surface than that which was subjected to high-temperature fire polishing with hydrogen, but fine irregularities are still left on the surface. The bending strength of the material thus treated was restored and improved to 10,000–12,000 kg/cm$^2$. When a molten salt of molybdate is used in place of that of borate, the material may be steeped in the molten salt at 1,200° C for about 20 minutes. When a molten salt of vanadium pentoxide is used, the material may be steeped in the molten salt at 1,400° C for about 10 minutes, with the same results obtained. In like manner, a molten salt of one of tungstate, lead oxide, and carbonate of sodium or potassium may be used.

(III-C) Combined use of high temperature chemical polishing with molten salt and high-temperature fire polishing with hydrogen For example, the single crystalline material after cutting and working was first subjected to high-temperature chemical polishing with molten salt under the same conditions as those in Item (III-B) and then subjected to high-temperature fire polishing with hydrogen under the same conditions as those in (III-A). The material thus treated becomes approximate in surface state to the single crystalline material shown left raised from the molten salt but is far more homogeneous and nothing irregular is noticed at all. And the bending strength of the material has been improved as high as to 15,000°–20,000 kg/cm$^2$. This strength is higher than the strength which the single crystal inherently has after it was raised from the molten salt, and is noteworthy in view of the fact that the bending strength of stainless steel is 10,000–12,000 kg/cm$^2$.

As described above, when the material is subjected to high-temperature chemical polishing with molten salt and/or high-temperature fire polishing with hydrogen, not only the sharp end edges of a somatic element can be removed but also the surface of the somatic element can be smoothened. Furthermore, the bending strength of the element can be improved by this very simple operation. Thus, the method of the invention is industrially far more advantageous than the mechanical grinding which requires stepwise reduction in the granuity of grindstone to obtain a smooth surface.

Now, a description will be made, with reference to the drawings, of embodiments wherein the somatic element of the invention is used in a dental implant and in an orthopedic surgical member for treating a broken bone.

EXAMPLE 1

A columnar single crystalline sapphire material obtained by the EFG process in Item (I) was cut and worked by the method described in Item (II) and was thereafter subjected to the removal of cutting scars by the method described in Item (III-C) by use of a borate polishing bath. The treatment thus carried out provided a flanged screw type implant member $i_1$, as shown in FIG. 1, having a smooth surface throughout the member. The implant member $i_1$ was formed on the circumference of its main body 1 to be set in a jawbone $b$ with threads 10 adapted to be threadedly inserted into a tap hole 5 formed in the jawbone $b$. The head 2 of the implant member $i_1$ is a part which serves as a part receiving a driving tool (not shown) when the member is threadedly inserted into the tap hole and which also serves as a part having an artificial tooth $t$ fitted thereover through an adhesive filler 4. The head 2 is worked into a hexagonal column. Furthermore, there is formed a disk-shaped horizontal flange 3 on the boundary circumference between the main body 1 and the head 2, said horizontal flange 3 being adapted to be tightly inserted into a counterbore 6 formed in the upper hard tissue $b_1$ when the implant member $i_1$ is threadedly inserted into the bone. The flange further serves as a stabilizing seat. Incidentally, in FIG. 1, reference character $f$ designates a mucous membrane of the gums (the same will apply in FIGS. 2 and 3); $b_2$ a soft tissue of the bone; and $b_3$ designates a hard tissue below the soft tissue (the same will apply also in FIGS. 2, 3 and 4$b$.

The flanged implant member $i_1$ is structurally improved in mechanical strength such that it can withstand the repeated outer force of occlusal impact. In addition, since it is made of a single crystalline sapphire material, the member $i_1$ is far higher in mechanical strength than a polycrystalline ceramic implant pin of the same shape and size. Even the main body 1 having a diameter of 3mm could sufficiently withstand repeated outer force, whereas there was a possibility of the polycrystalline ceramic implant pin being broken, depending upon the stress applied thereto. Roentgenoscopic observations made 6 months after the operation showed that no part of the member $i_1$ was broken or any movement was made of the member but that the tissue around the member $i_1$ fully proliferated and that the member was excellent in affinity with the tissue and there was no formation of a pocket caused by attenuation of a new bone tissue.

EXAMPLE 2

Figure 2:
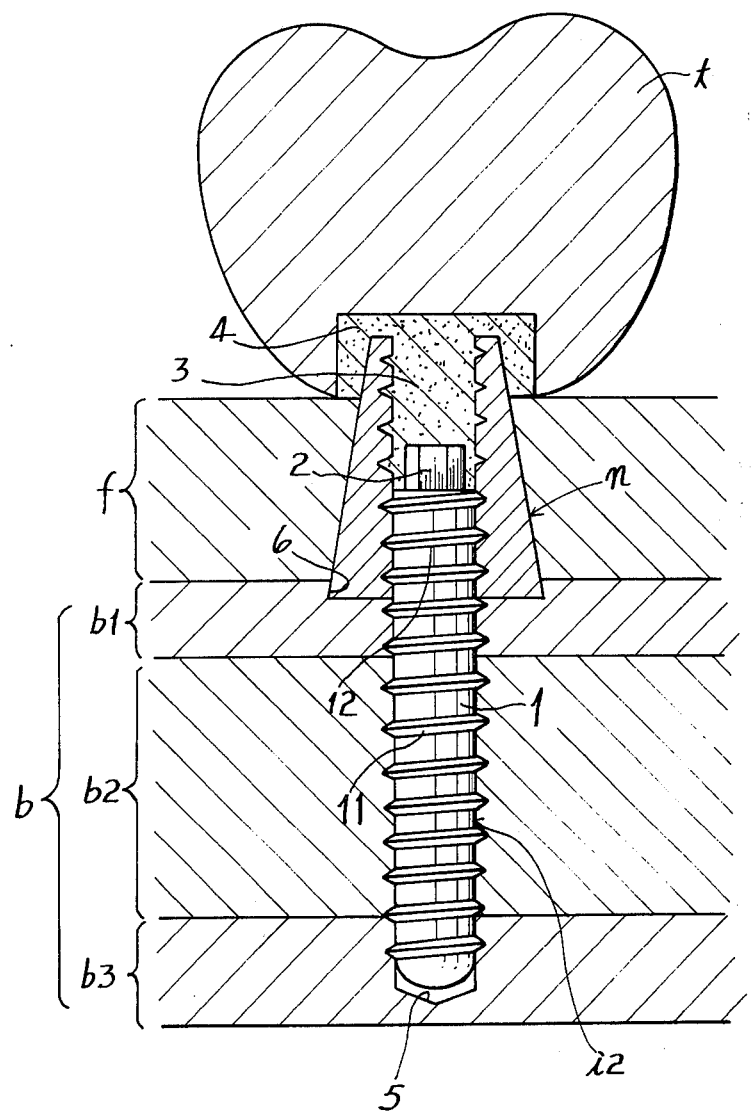
FIG. 2 is another sectional view showing a different embodiment of the element of the present invention as a dental implant.

A columnar screw type implant member $i_2$ having a smooth surface as shown in FIG. 2 was obtained by cutting and working a single crystalline sapphire material and removing the scars formed on the surface of the material by cutting and working from the surface of the implant member in the manner as in Example 1. The implant member $i_2$ obtained is formed with one continuous thread. The lower part of the thread being used as a threadedly mating part 11 adapted to be implanted in a tap hole 5 formed in the jawbone $b$ of the main body 1. The upper part of the thread being used as a threadedly mating part 12 adapted to receive a nut $n$ thereon in the exposed part above the upper surface of the jawbone $b$. The head 2 of the thread is machined into a hexagonal columnar form as a screw driving tool receiving part. The nut $n$ is made of polycrystalline alumina ceramics. The nut $n$ is threadedly fitted over the threaded part 12 of the main body 1 in the manner that the bottom of the nut comes into contact tightly with the bottom of the counterbore 6 formed on the upper surface of a hard tissue $b_1$ above the jawbone $b$. An artificial tooth $t$ is fitted over the nut $n$ through an adhesive filler 4 to thereby complete prosthetic operation.

Since the implant member $i_2$ described above is structurally designed to be fixed to the jawbone $b$ by screw tightening force of the nut $n$, it can sufficiently resist the outer force produced by occlusal impact. In addition, this implant member $i_2$, because it is made of a single crystalline sapphire material, can produce the same action and effect as that in Example 1.

EXAMPLE 3

Figure 3:
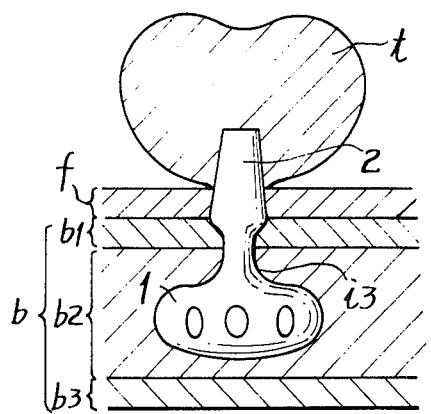
FIG. 3 is another sectional view of yet another embodiment of the element of the present invention used as a dental implant.

A plate-shaped single crystalline sapphire material obtained by the EFG process described in Item (I) was cut and worked by the process described in Item (II) and then the scars formed by the cutting and working were removed by the process described in Item (III-B) using a molybdate bath to obtain a blade type implant pin $i_3$ having a smooth surface throughout the surface thereon as shown in FIG. 3. This blade type implant pin was used for prosthetic purposes by passing a main body 1 through the mucous membrane $f$ of the gums, embedding the body 1 in the jawbone $b$ and fitting an artificial tooth $t$ over a sprout-shaped head 2.

According to roentgenoscopic observations 6 months after the operation performed, the tissue around the pin $i_3$ made good proliferation, and there was no movement of the pin $i_3$, much less any breakage of the pin.

EXAMPLE 4

Figure 4A:
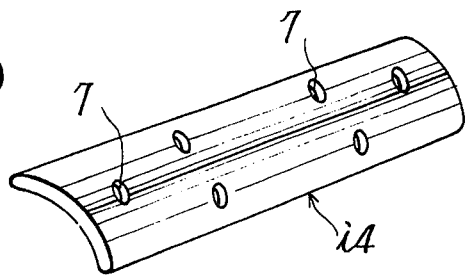
FIG. 4a is a perspective view of a compression plate.
Figure 4B:
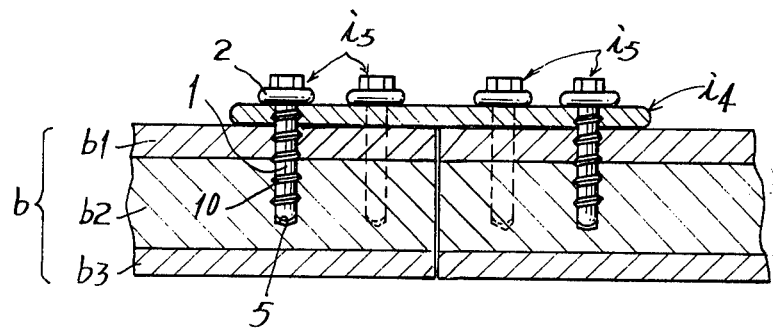
FIG. 4b is a sectional view showing the compression plate being applied to a broken bone.

A bent plate-shaped single crystalline sapphire material obtained by the EFG process described in Item (I) was cut and shaped, and the scars formed on the surface of the material by the cutting and shaping were removed by the process described in Item (III-A) to obtain a compression plate $i_4$ for the orthopedic treatment of a broken bone, the compression plate $i_4$ being smooth throughout the surface and being formed with pin passing holes 7, as shown in FIG. 4$a$. On the other hand, as shown in FIG. 4$b$, a screw type implant pin $i_5$ having an external thread 10 formed on a main body 1 and having a fitting portion for the reception of a hexagonal columnar driving tool formed on the head 2 thereof was obtained in the same manner as the implant $i_1$ in Example 1. The compression plate $i_4$ was applied to the circumference of a broken arm bone $b$ in the state of the broken part of the arm bone b being positioned end to end (with the least possible gap between both ends) and was fixed to the circumference by the screw type implant pin $i_5$ being threadedly inserted into tap holes formed in the arm bone b. According to roentgenoscopic observations made 6 months after the operation was performed, a bone tissue was gradually proliferated in the gap in the broken part. This demonstrates that the compression plate $i_4$ is naturally attached to the arm bone b despite any violent movement made by the arm bone. Furthermore, according to roentgenoscopic observations made one year after the operation, no sign was shown of the bone being attenuated in the bone tissue adjacent to the compression plate $i_4$ and screw type implant pin $i_5$ nor was there any trace of the pin $i_5$ being broken.

As will have been understood from the description and examples described and illustrated above, the invention can put such characteristic properties as mechanical strength inherent in a single crystal, excellence in flexibility and in affinity with an ambient tissue into full use, in that the invention uses single crystalline sapphire ceramics as a material for a somatic element, which material is shaped into a desired configuration and has its entire surface finished to a smooth surface by removing the sharp end edges and cut scars on the surface of the material. Accordingly, the somatic element according to the invention, even if it is as small as 3mm in diameter, which it was heretofore impossible to make a polycrystalline ceramics, can sufficiently withstand an outer force, thus making it possible to reduce the limitation on the area and design of an implant member to that degree.

In munching hard food, the jawbone also yields and in moving an arm, the arm bone also yields. But since the somatic element of the invention is excellent in flexibility, it also yields to a pressure of the kind described in response to such yielding of the jawbone and arm bone, with the result that the element is less liable to be broken. Furthermore, the somatic element of the invention entails no danger of development of bone cancer but is positively conductive to the proliferation of an ambient tissue because of the material used in the element being ceramics and because the element has no sharp end edge and is smooth on the surface. Also, the element is free from toxicity and hence it provides no possibility of such extracting of an implant member by reoperation as is the case with a somatic element made of metal.

I claim:

1. A somatic element for use as an implant in bone tissue and having good affinity with said bone tissue, said element comprising a single crystalline sapphire ceramic element having a bending strength of from about 9,000 to 20,000 kg/cm², said element being shaped into a desired implant configuration by cutting and working said element and further being smoothed by polishing such that said element is rendered substantially free from sharp edges and scars created by said cutting and working.

2. A somatic element according to claim 1 wherein said polishing comprises high-temperature chemical polishing with a molten salt.

3. A somatic element according to claim 1 wherein said polishing comprises high-temperature fire polishing at 1200°–1900° C in an atmosphere of reduced gas.

4. A somatic element according to claim 1 wherein said polishing includes both high-temperature chemical polishing with a molten salt and high-temperature fire polishing at 1200°–1900° C in an atmosphere of reduced gas.

5. A somatic element according to claim 1 wherein said somatic element is shaped into the configuration of a screw type endosseous implant member for dental surgery.

6. A somatic element according to claim 1 wherein said somatic element is shaped into a blade type endosseous implant member for dental surgery.

7. A somatic element according to claim 1 wherein said somatic element is shaped into a pin type endosseous implant member for dental surgery.

8. A somatic element according to claim 1 wherein said somatic element is shaped into a endosseous implant member for orthopedic surgery.

9. A somatic element according to claim 8 wherein said somatic element is shaped into a compression plate for orthopedic surgery.

* * * * *